US008464572B2

(12) United States Patent
Krolak et al.

(10) Patent No.: US 8,464,572 B2
(45) Date of Patent: Jun. 18, 2013

(54) IN-SITU SENSOR FOR AUTOMATED MEASUREMENTS OF GAS CONTENT IN LIQUID AND RELATED SYSTEM AND METHOD

(75) Inventors: Adam Krolak, North Vancouver (CA); Reena Meijer Drees, New Westminster (CA); Frank M. Haran, North Vancouver (CA); Sebastien Tixier, North Vancouver (CA)

(73) Assignee: Honeywell ASCA Inc., Mississauga, Ontario (CA)

( * ) Notice: Subject to any disclaimer, the term of this patent is extended or adjusted under 35 U.S.C. 154(b) by 308 days.

(21) Appl. No.: 12/899,707

(22) Filed: Oct. 7, 2010

(65) Prior Publication Data

US 2012/0085144 A1    Apr. 12, 2012

(51) Int. Cl.
G01N 33/18    (2006.01)

(52) U.S. Cl.
USPC ......................................................... 73/19.1

(58) Field of Classification Search
USPC .................... 73/19.1, 19.01; 356/436, 437
See application file for complete search history.

(56) References Cited

U.S. PATENT DOCUMENTS

| 5,132,094 | A | 7/1992 | Godec et al. | |
|---|---|---|---|---|
| 6,939,717 | B2 * | 9/2005 | Jiang et al. | 436/121 |
| 7,263,246 | B1 | 8/2007 | Duan et al. | |
| 7,330,262 | B2 * | 2/2008 | Siepmann et al. | 356/441 |
| 2005/0247574 | A1 | 11/2005 | Varney | |
| 2009/0128818 | A1 * | 5/2009 | Goodwin et al. | 356/436 |
| 2010/0302546 | A1 * | 12/2010 | Azimi et al. | 356/437 |

OTHER PUBLICATIONS

Robert O'Leary, et al., "Attenuated Total Reflection Spectroscopy method for measuring dissolved CO2 concentration in Beer", VitalSensors Technologies, LLC, 4 pages, (No Date).
"GMP343 Carbon Dioxide Probe for Demanding Measurements", Vaisala, 2009, 2 pages.
"Vaisala CARBOCAP Carbon Dioxide Probe GMP343", User's Guide, Vaisala, 2007, 96 pages.
"OxyGuard CO2 Portable, Portable Dissolved CO2 Analyser", OxyGuard, 2 pages, (No Date).
"InPro 5000 CO2 Sensors, Instruction manual", Mettler Toledo, Sep. 2006, 19 pages.
"GM70 Hand-Held Carbon Dioxide Meter for Spot-Checking Applications", Vaisala, 2009, 2 pages.
"GMD/W20 Series Carbon Dioxide Transmitters for Demand Controlled Ventilation Applications", Vaisala, 2009, p. 96-97.
"GMM111 Carbon Dioxide Module", Vaisala, 2009, 2 pages.
"GMM2OW CO2 module", Vaisala, Nov. 16, 1999, 5 pages.

(Continued)

Primary Examiner — Daniel Larkin
Assistant Examiner — Jamar Ray (57) ABSTRACT

A system includes a signal source that provides a first signal for measuring a gas content of a liquid sample. The system also includes an analyzer that determines the gas content of the liquid sample using a measurement of a second signal, where the second signal is based on the first signal. The system further includes an apparatus with a walled structure having a cavity. The apparatus also includes a piston that pulls the liquid sample into the cavity and pushes the liquid sample out of the cavity. The apparatus further includes at least one measurement window having at least one inner surface exposed within the cavity. The at least one measurement window receives the first signal from the signal source and provides the second signal to the analyzer. The piston could also clean the at least one inner surface, and the piston can include a reference material for calibrating the analyzer.

20 Claims, 6 Drawing Sheets

OTHER PUBLICATIONS

"GMM220 Carbon Dioxide Modules for Demanding OEM Applications", Vaisala, 2010, 2 pages.

"GMT220 Series Carbon Dioxide Transmitters for Industrial Applications", Vaisala, 2009, 2 pages.

"GMW115 Carbon Dioxide Transmitter for Demand-controlled Ventilation", Vaisala, 2009, 2 pages.

"SenseAir, Product Specification, CO2 Engine K22-OC", May 4, 2007, 8 pages.

"SenseAir, Product Description, CO2 Engine K30, Sensor module and OEM platform", 12 pages, (No Date).

"SenseAir, Product Description, CO2 Engine-BLG/ELG, Sensor module for environment parameters logging", 13 pages, (No Date).

"Life Sciences products", YSI, 21 pages, (No Date).

"Pipette calibration specials", www.johnmorris.com.au, 4 pages, (No Date).

"Transmitter CO2 5100 e, Sensor InPro 5000, CO2 measuring systems for fermentation control, Technical data", Mettler Toledo, 12 pages, Sep. 2006.

\* cited by examiner

IN-SITU SENSOR FOR AUTOMATED MEASUREMENTS OF GAS CONTENT IN LIQUID AND RELATED SYSTEM AND METHOD

TECHNICAL FIELD

This disclosure relates generally to gas sensors. More specifically, this disclosure relates to an in-situ sensor for automated measurements of gas content in liquid and related system and method.

BACKGROUND

It is often necessary or desirable to identify the gas content in a liquid. For example, it may be desirable to measure the carbon dioxide or oxygen content in water, where the measurements are used to help promote plant or animal growth in the water. As a particular example, algae can be used to produce biofuels, and the carbon dioxide content of water in which the algae grows can be measured and controlled. Ideally, carbon dioxide measurements can be used to determine how to treat the water in order to increase or maximize algae growth.

Various types of gas sensors have been developed, but they usually suffer from one or more drawbacks. For example, non-dispersive infrared (NDIR) spectroscopic sensors have been used to measure gas content in air. However, direct measurements of gas content in liquid using an NDIR spectroscopic sensor are difficult. This is due to a number of factors, such as the high attenuation of liquid.

Gas sensors with sensitive polymer-based membranes have also been used to measure the gas content in liquid. However, these sensors can suffer from short-term and long-term drift and may therefore require frequent calibration. Also, the polymer-based membranes can become soiled by contaminants and may require frequent cleaning. In addition, these types of membranes typically have low overall lifetimes, meaning the membranes need frequent replacement.

SUMMARY

This disclosure provides an in-situ sensor for automated measurements of gas content in liquid and related system and method.

In a first embodiment, a system includes a signal source configured to provide a first signal for measuring a gas content of a liquid sample. The system also includes an analyzer configured to determine the gas content of the liquid sample using a measurement of a second signal, where the second signal is based on the first signal. The system further includes an apparatus with a walled structure having a cavity and a piston configured to (i) pull the liquid sample into the cavity and (ii) push the liquid sample out of the cavity. The apparatus also includes at least one measurement window having at least one inner surface exposed within the cavity. The at least one measurement window is configured to (i) receive the first signal from the signal source and (ii) provide the second signal to the analyzer.

In a second embodiment, an apparatus includes a walled structure having a cavity. The apparatus also includes a piston configured to (i) pull a liquid sample into the cavity and (ii) push the liquid sample out of the cavity. The apparatus further includes at least one measurement window having at least one inner surface exposed within the cavity. The at least one measurement window is configured to (i) receive a first signal for measuring a gas content of the liquid sample and (ii) provide a second signal based on the first and the gas content of the liquid sample.

In a third embodiment, a method includes pulling a liquid sample into a cavity of a sensor using a piston. The method also includes providing a first signal from a signal source into the cavity using at least one measurement window. The at least one measurement window has at least one inner surface exposed within the cavity. The method further includes providing a second signal to an analyzer using the at least one measurement window, where the second signal is based on the fist signal and a gas content of the liquid sample. In addition, the method includes pushing the liquid sample out of the cavity using the piston.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 5, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
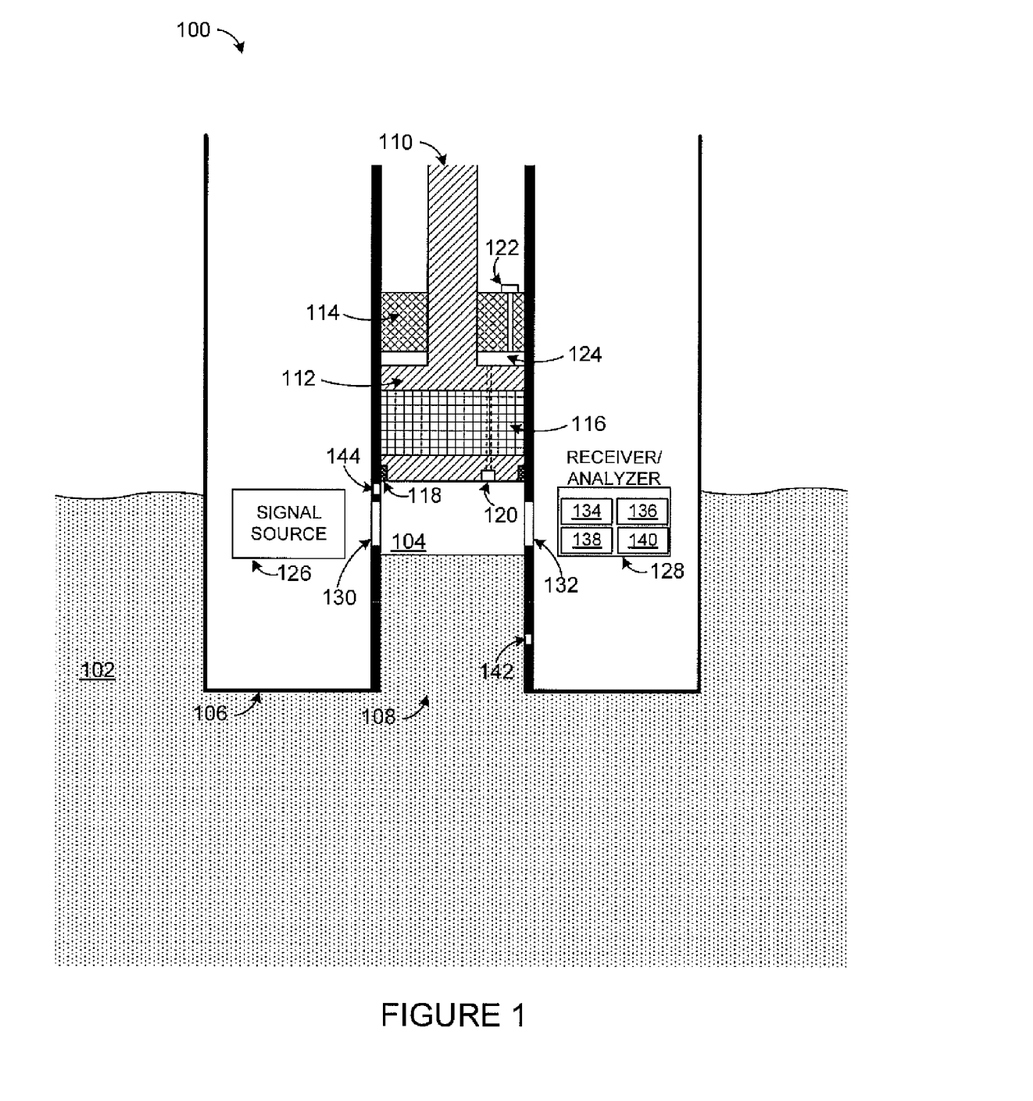
FIG. 1 illustrates an example in-situ sensor for automated measurements of gas content in liquid according to this disclosure.

FIG. 1 illustrates an example in-situ sensor 100 for automated measurements of gas content in liquid according to this disclosure. In this example, the sensor 100 is partially submerged into a liquid 102. The sensor 100 measures the gas content in the liquid 102 by pulling a sample of the liquid 102 into the sensor 100. A head space 104 is created above the sample, where the head space 104 is filled with atmospheric or other air. By taking measurements of the air in the head space 104, the sensor 100 can determine the gas content in the sample of the liquid 102. The sample of the liquid 102 and the air in the head space 104 can then be expelled from the sensor 100, and a new sample of the liquid 102 can be obtained. Periodically (such as during each measurement cycle), the sensor 100 can be cleaned and calibrated to help ensure accurate measurements.

Any suitable gas content of any suitable liquid 102 could be measured using the sensor 100. For example, the sensor 100 could measure the concentration of oxygen, carbon dioxide, or any other or additional gas(es) in water or any other or additional liquid(s). The sensor 100 could also detect the presence or measure the concentration of a volatile material in an industrial liquid. The sensor 100 could further form part of a larger system that operates based on sensor measurements from the sensor 100. For instance, the sensor 100 could be used in conjunction with an algae pond in which algae is grown for use in biofuel production. The sensor 100 could also be used in conjunction with a carbon dioxide sequestration system in which carbon dioxide is sequestered. The sensor 100 could further be used in an industrial control and automation system in which the gas content in liquid can be measured and used to adjust an industrial process. In addition, the sensor 100 could be used in a safety monitoring system in which the gas content in liquid can be measured and used for threshold monitoring. Any other or additional system where the gas content in a liquid is measured could be used.

As shown in FIG. 1, the sensor 100 includes an outer walled structure 106 that defines a cavity generally referred to as a guide tube 108. The outer structure 106 represents a housing or other structure that can encase or otherwise protect other components of the sensor 100. The guide tube 108 represents any suitable cavity into which a sample of the liquid 102 can be obtained and released. The guide tube 108 could, for instance, represent a cylindrical cavity in the housing of the sensor 100.

A piston 110 travels up and down within the guide tube 108. Movement of the piston 110 can be controlled using appropriate components (not shown). In this example, the piston 110 includes a piston head 112, which generally can be lowered to a bottom of the guide tube 108 and raised to a flange 114. This allows the piston 110 to pull a sample of liquid 102 into a lower portion of the guide tube 108 and to push the sample of liquid 102 out of the guide tube 108.

As shown in FIG. 1, the piston head 112 includes a reference material 116, a seal 118, and a valve 120. As described below, the reference material 116 allows radiation or other signals to pass through the piston head 112 during calibration of the sensor 100. The reference material 116 could be formed from any suitable material(s), which can depend on the type of signals used during sensor measurements. For instance, when infrared radiation is used (such as 4.2 µm radiation), the reference material 116 could be formed from quartz, sapphire, glass, or calcium fluoride. The reference material 116 could be a permanent internal part of the piston head 112 (although that need not be the case).

The seal 118 helps to prevent air, liquid, or other material from passing between the piston head 112 and the inner surface of the guide tube 108. Also, as described below, the seal 118 can help to clean the inner surface of the guide tube 108. The seal 118 includes any suitable structure for substantially preventing passage of material between two structures. The seal 118 could, for example, include one or more O-rings.

The valve 120 in the piston head 112 and a valve 122 in the flange 114 are used to create the head space 104 above the sample of the liquid 102 in the guide tube 108. For example, the valve 122 can be opened and later closed to trap atmospheric or other air in a space 124 above the piston head 112. The valve 120 can allow the trapped air to move below the piston head 112, forming the head space 104. Additional details regarding the operation of the valves 120-122 are provided below. Each valve 120-122 includes any suitable structure for controlling flow of air. For instance, the valve 120 may represent an uncontrolled one-way valve, and the valve 122 may represent a controllable bidirectional valve.

Measurements of the air in the head space 104 and reference measurements of the reference material 116 are taken using a signal source 126 and a receiver/analyzer 128. The signal source 126 generates signals (such as infrared radiation, visible radiation, or acoustic waves) that pass through a window 130, the material within the guide tube 108, and a window 132. The receiver/analyzer 128 receives and measures the signals that have interacted with the material in the guide tube 108. The receiver/analyzer 128 can analyze the measurements to either calibrate the sensor 100 or identify the gas content in the sample of the liquid 102.

The signal source 126 includes any suitable structure for providing signals for measuring gas content of material, such as a radiation source that provides radiation at one or more desired wavelengths or wavelength bands. The signal source 126 could, for example, include a quartz tungsten halogen lamp, one or more light emitting diodes (LEDs), or one or more laser diodes that emit light at the appropriate wavelength(s) or wavelength band(s).

The receiver/analyzer 128 includes any suitable structure for receiving and analyzing signals that have interacted with material in order to identify a gas content in a liquid sample. For instance, the receiver/analyzer 128 could include a detector 134 that measures one or more characteristics of radiation or other signals received through the window 132. The detector 134 could represent a photodetector, spectrometer, or other detection mechanism. The receiver/analyzer 128 could also include a processing unit 136 that analyzes the measurements obtained by the detector 134 to determine the gas content in the liquid sample. The processing unit 136 could include a microprocessor, microcontroller, digital signal processor (DSP), field programmable gate array (FPGA), application specific integrated circuit (ASIC), or other processing device. The receiver/analyzer 128 could further include a memory unit 138 that stores instructions and data used, generated, or collected by the processing unit 136. The memory unit 138 could include any suitable volatile and/or non-volatile storage and retrieval device(s). In addition, the receiver/analyzer 128 could include an interface 140 for transmitting data (such as determined gas contents) to an external device or system or for receiving data (such as configuration data). The interface 140 could represent any suitable wired or wireless interface(s), such as a wired Ethernet interface or a wireless radio frequency (RF) transceiver.

Although not shown, the signal source 126 and the receiver/analyzer 128 could be placed in location(s) apart from the windows 130-132. Optical fibers or other structures could then be used to transport signals from the signal source 126 to the window 130 and to transport signals from the window 132 to the receiver/analyzer 128. In fact, the signal source 126 and the receiver/analyzer 128 could reside outside of the walled structure 106 and might not even form part of the sensor structure.

Each of the windows 130-132 represents any suitable structure through which radiation or other signals from the signal source 126 can pass. The windows 130-132 could be completely or substantially transparent to the signals from the signal source 126. Each of the windows 130-132 could, for example, be formed from quartz, sapphire, glass, calcium fluoride, or other suitable material(s).

Optionally, one or more sensors can be used in or with the in-situ gas sensor 100 to support measurements of the gas content in the liquid sample. For example, a sensor 142 could be used to measure the temperature of the liquid sample. One or more sensors 144 could be used to measure the temperature and pressure of the head space 104. Measurements from the sensors 142-144 could be provided to the receiver/analyzer 128 for use in determining the gas content in the liquid sample. Each sensor 142-144 includes any suitable structure for measuring a temperature, pressure, or other characteristic(s) of liquid or air. While the sensors 142-144 are shown as embedded within the walled structure 106, the sensors 142 and/or 144 could reside at any other suitable location(s). For instance, pressure and temperature sensors could be embedded within the bottom surface of the piston head 112. In other embodiments, the pressure inside the head space 104 can be controlled to a specific known value, and only the temperatures of the head space 104 and liquid sample could be measured.

FIGS. 2A through 2D illustrate an example use of the in-situ sensor 100 from FIG. 1 according to this disclosure. Various reference numerals unnecessary for an understanding of how the sensor 100 operates may be omitted in individual figures.

Figure 2A:
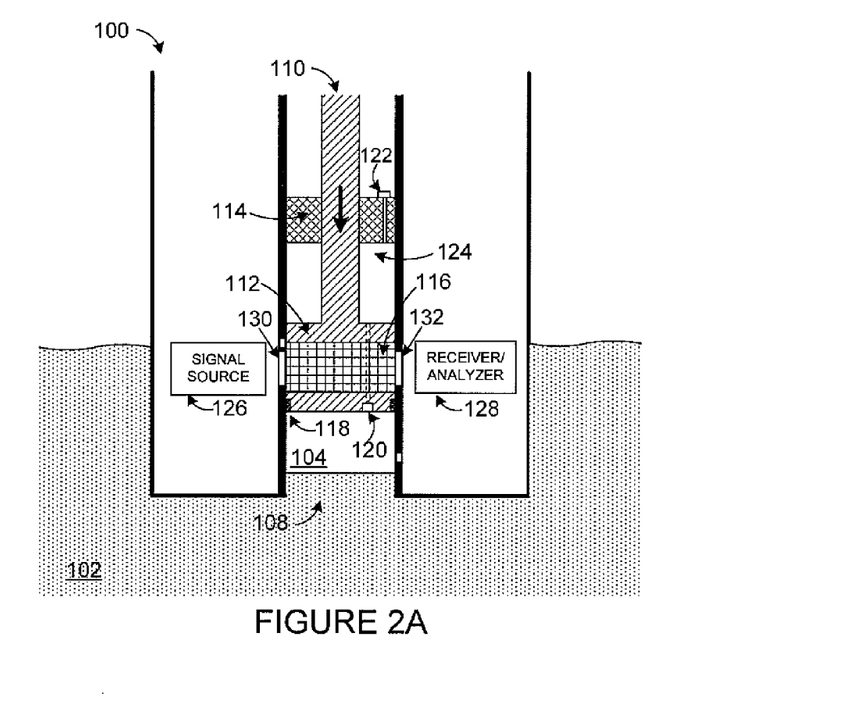
FIGS. 2A through 2D illustrate an example use of the in-situ sensor from FIG. 1 according to this disclosure.

In one aspect of operation, the sensor 100 takes measurements of the gas content in the liquid 102 during multiple measurement cycles. The measurement cycles could be continuous, near-continuous, periodic at a specified interval, or aperiodic (such as in response to an external command). A measurement cycle could begin as shown in FIG. 2A, where the piston 110 is being pushed down to expel a prior sample of the liquid 102 from the guide tube 108. The valve 122 can be opened during this time, which allows fresh air to be pulled into the space 124 above the piston head 112 and below the flange 114.

As the piston head 112 moves down, the seal 118 passes along the interior surface of the guide tube 108. As a result, the seal 118 can push air bubbles, material, and other contaminants off the surface of the guide tube 108, helping to clean the guide tube 108. Among other things, this can help to remove contaminants from the inner surface of the windows 130-132.

At some point, the reference material 116 in the piston head 112 aligns with the windows 130-132, and signals from the signal source 126 can pass through the reference material 116. These signals can be measured by the receiver/analyzer 128 and analyzed in order to calibrate the sensor 100. This calibration could occur during each measurement cycle, meaning each time a new sample of liquid 102 is pulled into the guide tube 108 and analyzed. Note, however, that the calibration could occur at other times, such as at a longer interval.

Figure 2B:
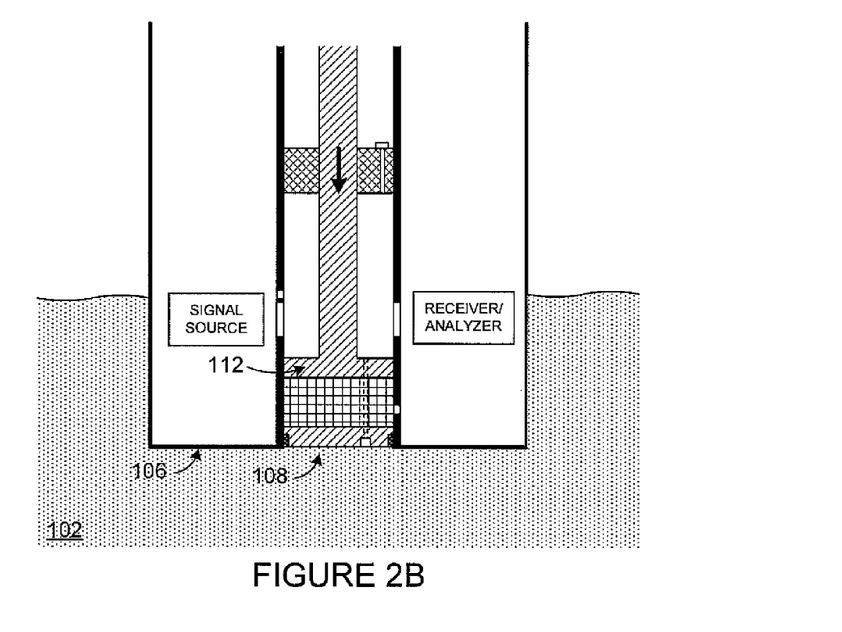

As shown in FIG. 2B, the piston head 112 can continue to be pushed down until the prior sample of the liquid 102 and the air in its associated head space 104 are pushed out of the guide tube 108. Note that while the bottom of the piston head 112 is shown as being flush with the bottom of the structure 106, this may not be the case. At this point, the sensor 100 may immediately begin to draw a new liquid sample into the guide tube 108 by raising the piston head 112. Alternatively, some time may elapse before the piston head 112 is raised.

Figure 2C:
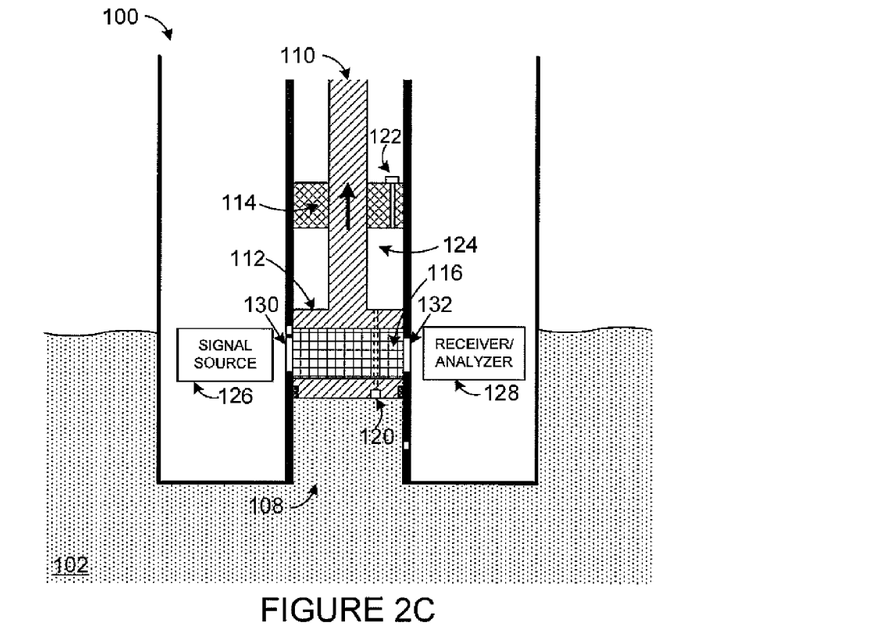

FIG. 2C shows the raising of the piston head 112, which draws a new sample of the liquid 102 into the guide tube 108. During this time, the valve 122 may remain open, allowing some of the air in the space 124 to escape through the flange 114. Note that the reference material 116 of the piston head 112 again aligns with the windows 130-132 during this movement, and calibration could optionally occur here instead of (or in addition to) the calibration performed during the alignment shown in FIG. 2A.

Figure 2D:
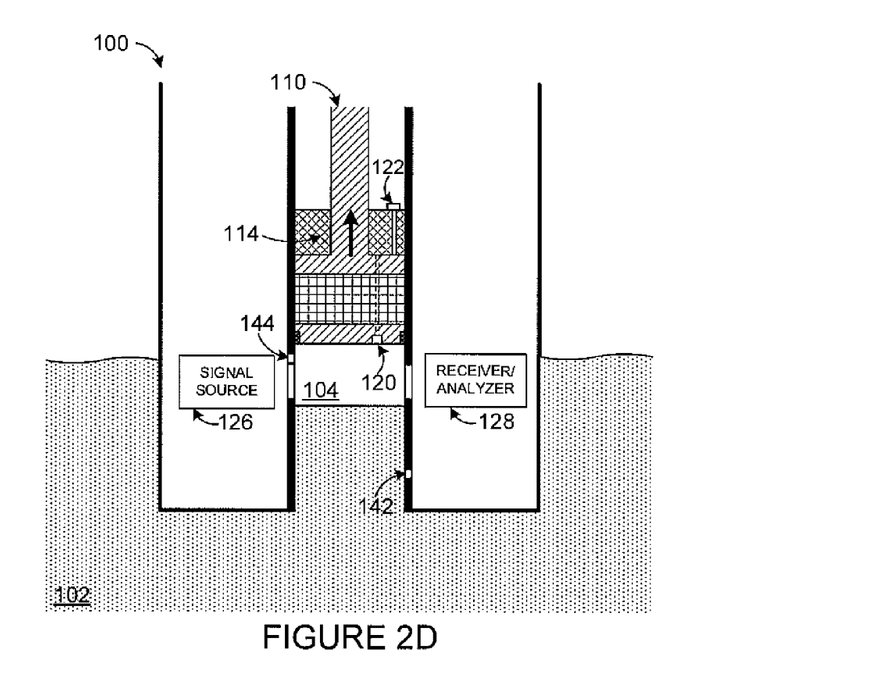

At some specified position of the piston head 112, the valve 122 closes to trap air in the space 124. This could occur during upward movement of the piston head 112, although it could occur at other times. When the valve 112 is closed, the upward movement of the piston head 112 forces the air trapped in the space 124 to flow through the valve 120 and form the head space 104 as shown in FIG. 2D. A measurement of the gas content in the liquid sample can then occur using the signal source 126 and the receiver/analyzer 128, where signals from the signal source 126 pass through the air in the head space 104. When that measurement is complete, the sensor 100 could begin another measurement cycle.

The sensor 100 could use any suitable technique to measure gas content in the liquid sample by passing signals through the air in the head space 104 above the liquid sample. For example, a gas in the liquid sample could diffuse into the head space 104 (or vice versa) until an equilibrium is reached between the gas in the liquid sample and the gas in the head space 104. The equilibrium need not involve equal content in the head space 104 and the liquid sample. Rather, the equilibrium depends, among other things, on the nature of the gas, the pressure and temperature of the air inside the head space 104, and the temperature of the liquid sample. The signals received by the receiver/analyzer 128 can be used to measure the content of the gas in the head space 104, such as by using a non-dispersive infrared (NDIR) spectroscopic technique. If the temperature and pressure within the head space 104 and the temperature of the liquid sample are known (such as via the sensors 142-144), the measured content of the gas in the head space 104 can be used to estimate the content of the same gas in the liquid sample.

The sensor 100 can provide various advantages depending on its implementation. For example, measurements can be obtained by the sensor 100 in-situ, meaning the sensor 100 can be placed in a specific location and generate gas content readings at that location. Also, samples of the liquid 102 can be automatically collected and removed from the sensor 100, so there is no need for complex sample preparation and transport mechanisms. Further, sensor calibration can be automatically performed frequently, such as during each measurement cycle. This can help to ensure greater short-term and long-term stability of the sensor measurements. Moreover, the sensor's inlet (at the bottom of the guide tube 108) and the windows 130-132 can be cleaned to remove bio-film, gas bubbles, dirt, or other contaminants during each measurement cycle. In addition, measurements can be done in a controlled environment with full sample exchange during each measurement cycle, which can help to ensure accurate sensor measurements.

Although FIG. 1 illustrates one example of an in-situ sensor 100 for automated measurements of gas content in liquid and FIGS. 2A through 2D illustrate its use, various changes may be made to FIGS. 1 and 2A through 2D. For example, the shapes and relative sizes of the components in the sensor 100 are for illustration only. Also, the positions of various components in the sensor 100 could be modified according to particular needs. In addition, the measurement cycle shown in FIGS. 2A through 2D could start with any other suitable position of the piston head 112, such as at the bottom of the guide tube 108.

Figure 3:
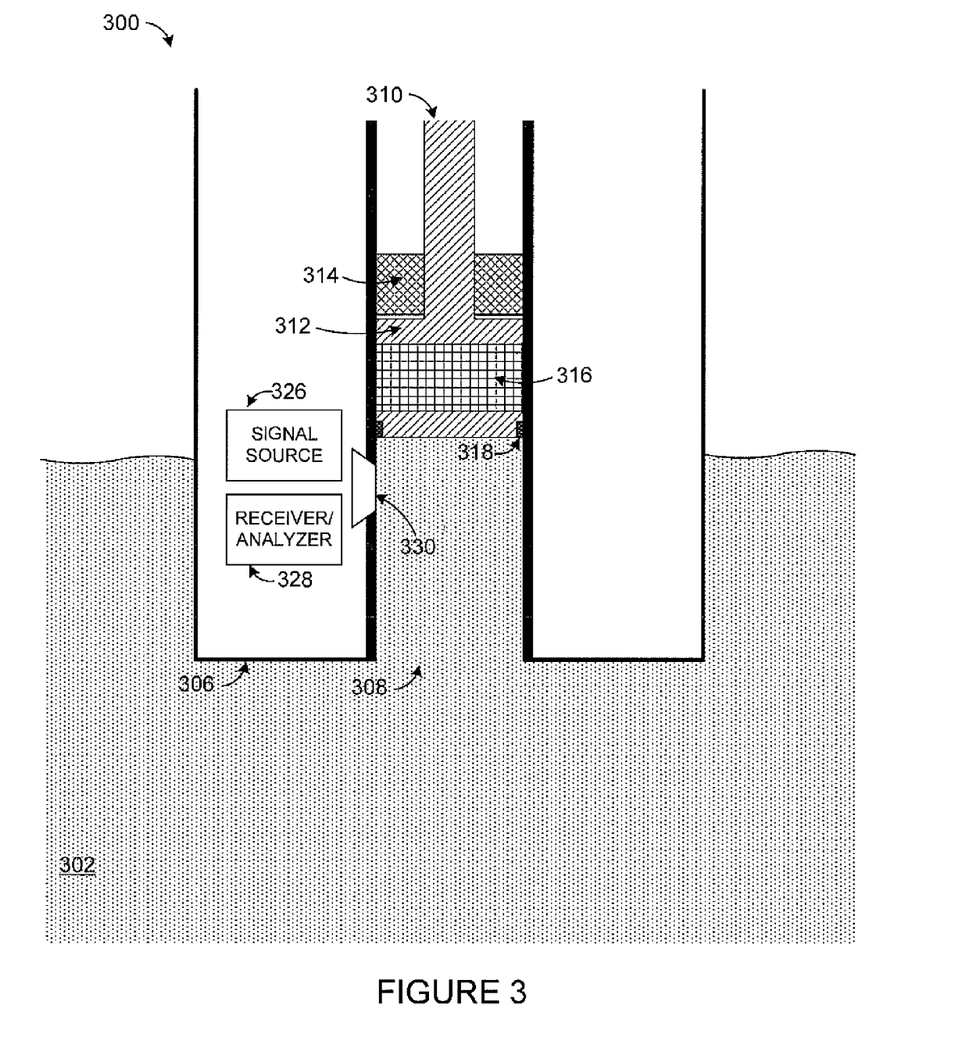
FIG. 3 illustrates another example in-situ sensor for automated measurements of gas content in liquid according to this disclosure.

FIG. 3 illustrates another example in-situ sensor 300 for automated measurements of gas content in liquid according to this disclosure. The structure of the sensor 300 is similar to the structure of the sensor 100. The sensor 300 is used to obtain a sample of a liquid 302 and to measure the gas content of the liquid 302 directly. The sensor 300 includes an outer structure 306 with a guide tube 308 in which samples of the liquid 302 are held. The sensor 300 also includes a piston 310 with a piston head 312 and a flange 314. The piston head 312 includes a reference material 316 and a seal 318.

In this example, a signal source 326 and a receiver/analyzer 328 are located on a common side of the sensor 300, and a single window 330 is used by the signal source 326 and the receiver/analyzer 328. In some embodiments, the window 330 represents an Attenuated Total Reflection (ATR) spectroscopy crystal mounted at least partially within the guide tube 308, where an inner surface of the crystal is exposed to the liquid sample.

During an ATR measurement, radiation (such as infrared light) is provided from the signal source 326 to the ATR crystal or other window 330. The radiation is internally reflected off the inner surface of the window 330 at least one time, where the inner surface of the window 330 forms an interface with the liquid sample. During the at least one reflection, a small portion of the radiation propagates into the liquid sample as evanescent waves. The remaining radiation exits the window 330 and is received by the receiver/analyzer 328. Given a suitable wavelength of radiation, the amount of radiation that propagates into the liquid sample is dependent on the gas concentration for a particular gas in the sample. As a result, the receiver/analyzer 328 can measure the attenuation of the received radiation to identify a particular gas' content in the liquid sample.

The reference material 316 used here may have good optical contact with the window 330 when moved past the window 330 by the piston 310. This good optical contact could help to ensure that the sensor 300 is accurately calibrated. Example reference materials 316 could include pure water, a soft polymer, or other material that is stable over time.

The sensor 300 could have a measurement cycle similar to that shown in FIGS. 2A through 2D above. The piston head 312 can be lowered to push a prior sample of liquid 302 out of the guide tube 308, and the piston head 312 can be raised to pull a new sample of liquid 302 into the guide tube 308. During the lowering and/or raising of the piston head 312, the reference material 316 can be used to calibrate the sensor 300. Also, during the lowering of the piston head 312, cleaning can be done by the seal 318 of the piston head 312 pushing contaminants off the inner surface of the guide tube 308, including off the inner surface of the measurement window 330. Note that a measurement cycle could start with the piston head 312 at any other suitable location.

Once again, this type of sensor 300 can offer various advantages depending on its implementation. In addition to the advantages discussed above, the sensor 300 could be thinner due to the co-location of the signal source 326 and the receiver/analyzer 328. Also, the sensor 300 can measure gas content directly in a liquid without the need for valves or other components to create a head space.

Although FIG. 3 illustrates another example of an in-situ sensor 300 for automated measurements of gas content in liquid, various changes may be made to FIG. 3. For example, the shapes and relative sizes of the components in the sensor 300 are for illustration only. Also, the positions of various components in the sensor 300 could be modified according to particular needs. As a particular example, the signal source 326 and the receiver/analyzer 328 could be moved to other location(s), and optical fibers or other structures could be used to provide signals to and receive signals from the window 330.

Figure 4:
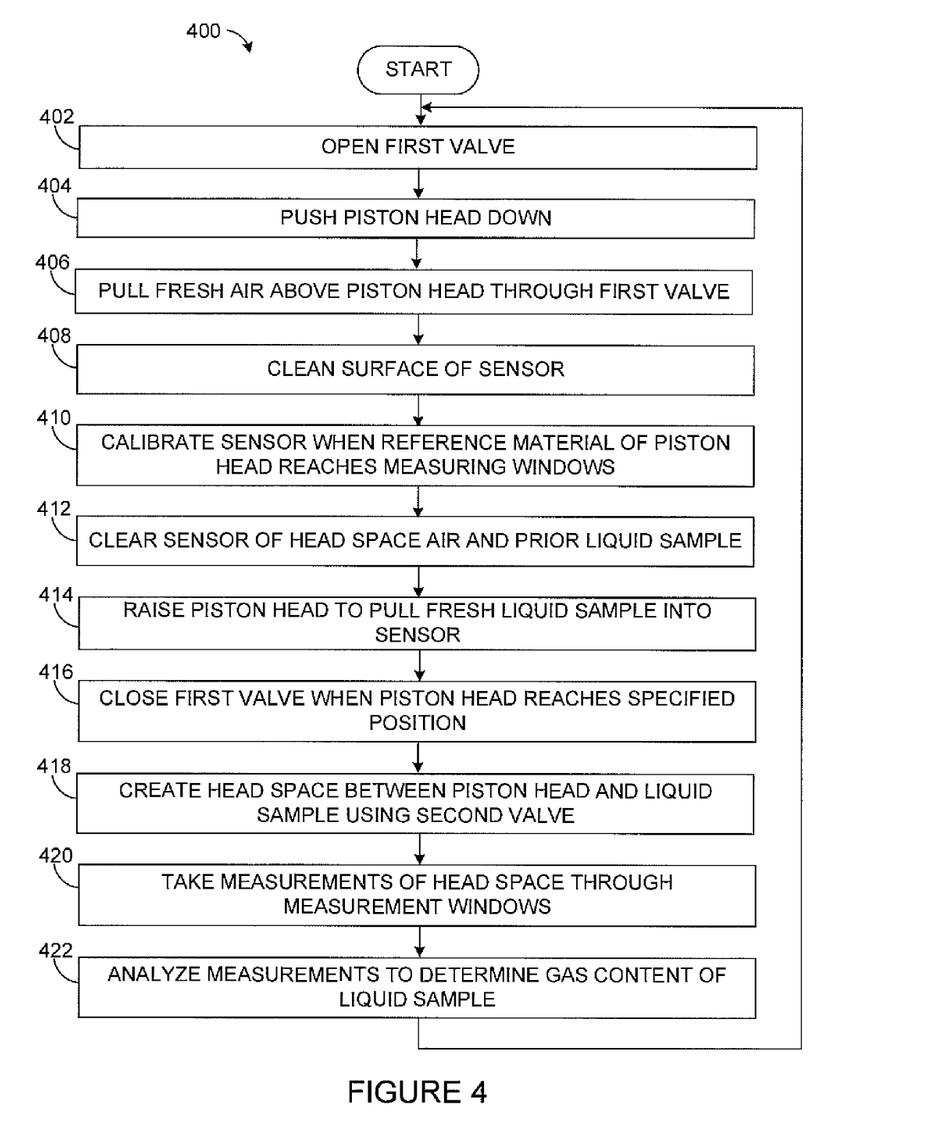
FIGS. 4 and 5 illustrate example methods for automated measurements of gas content in liquid using in-situ sensors according to this disclosure.
Figure 5:
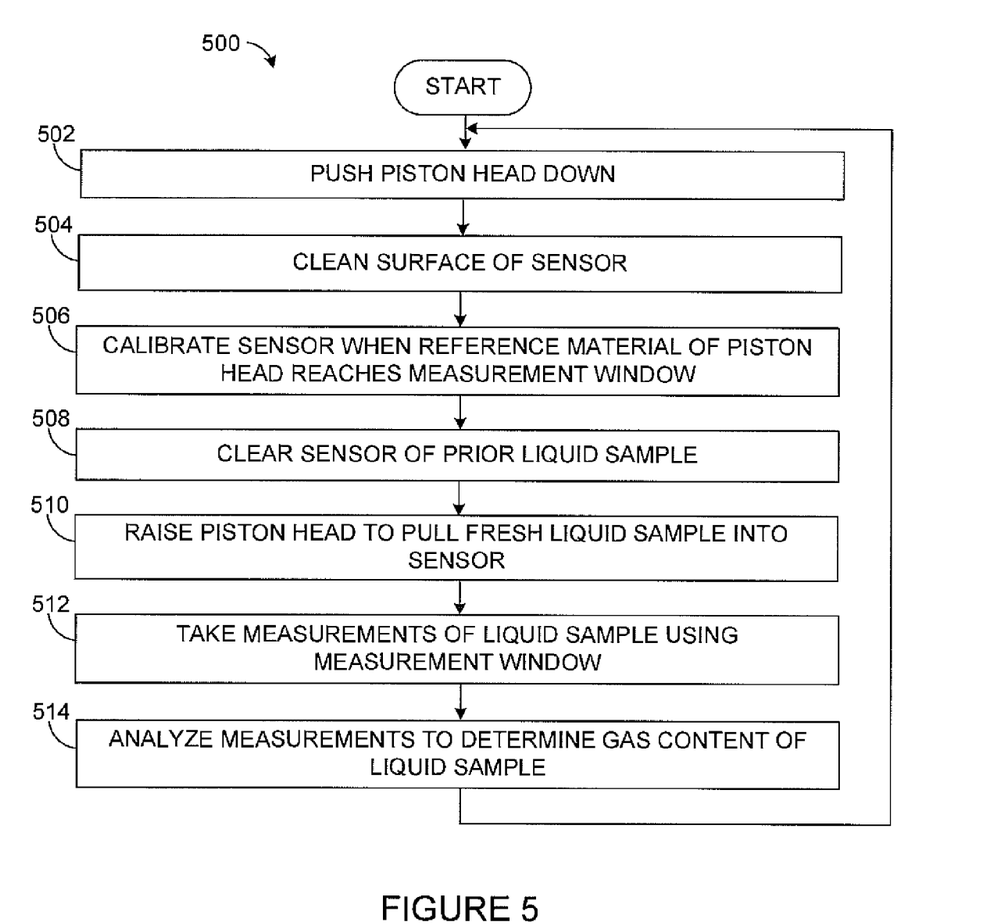

FIGS. 4 and 5 illustrate example methods 400 and 500 for automated measurements of gas content in liquid using in-situ sensors according to this disclosure. The method 400 is described with respect to the sensor 100 of FIG. 1, and the method 500 is described with respect to the sensor 300 of FIG. 3. The same or similar methods could be used with any other suitable sensors.

As shown in FIG. 4, a first valve is opened at step 402, and a piston head is pushed down at step 404. This could include, for example, opening the valve 122 and pushing the piston head 112 down. Fresh air is pulled into the sensor above the piston head through the first valve at step 406. This could include, for example, fresh air being pulled into the space 124 above the piston head 112.

A surface of the sensor is cleaned at step 408, the sensor is calibrated at step 410, and the sensor is cleared of head space air and a prior liquid sample at step 412. The cleaning can be done by the seal 118 of the piston head 112 pushing contaminants off the inner surface of the guide tube 108, including off the inner surfaces of the measurement windows 130-132. The calibration can be performed when the reference material 116 of the piston head 112 reaches the windows 130-132 of the sensor 100. The calibration could involve the signal source 126 providing radiation, acoustic waves, or other signals through the reference material 116. Clearing the sensor of head space air and the prior liquid sample could include the piston head 112 pushing the prior sample of the liquid 102 and its associated head space 104 out of the guide tube 108.

The piston head is raised to pull a fresh sample of liquid into the sensor at step 414. This could include, for example, raising the piston head 112 to pull a new sample of the liquid 102 into the guide tube 108. The first valve is closed when the piston head reaches a specified position at step 416, and a head space is created between the new liquid sample and the piston head at step 418. This could include, for example, closing the valve 122 to trap air in the space 124 above the piston head 112. This could also include forcing the trapped air through a one-way valve 120 or other structure to create the head space 104 below the piston head 112.

Measurements of the head space are taken through the measurement windows at step 420, and the measurements are analyzed to determine a gas content of the liquid sample at step 422. This could include, for example, the signal source 126 sending signals through the window 130, the air in the head space 104, and the window 132 to the receiver/analyzer 128. This could also include the receiver/analyzer 128 performing calculations to identify the gas content of the liquid sample using measurements of the signals received through the window 132. As a particular example, this could include the receiver/analyzer 128 using NDIR or other techniques to identify the gas content of the head space 104 and then using the temperature and pressure in the head space 104 and the temperature of the liquid sample to identify the gas content in the liquid sample.

As shown in FIG. 5, a piston head is pushed down at step 502. This could include, for example, pushing the piston head 312 down within the guide tube 308. A surface of the sensor is cleaned at step 504, the sensor is calibrated at step 506, and the sensor is cleared of a prior liquid sample at step 508. The cleaning can be done by the seal 318 of the piston head 312 pushing contaminants off the inner surface of the guide tube 308, including the inner surface of the measurement window 330. The calibration can be performed when the reference material 316 of the piston head 312 reaches the window 330. Note that any other calibration method can be used, including internal calibration or verification mechanisms in the signal source and receiver/analyzer. Clearing the sensor of the prior liquid sample could include the piston head 312 pushing the prior sample of the liquid 302 out of the guide tube 308.

The piston head is raised to pull a fresh sample of liquid into the sensor at step 510. This could include, for example, raising the piston head 312 to pull a new sample of liquid 302 into the guide tube 308. Measurements of the liquid sample are taken using the measurement window at step 512, and the measurements are analyzed to determine a gas content of the liquid sample at step 514. This could include, for example, the signal source 326 providing signals to the window 330. This could also include the receiver/analyzer 328 performing calculations to identify the gas content of the liquid sample using measurements of the signals received from the window 330. As a particular example, this could include the receiver/analyzer 328 using ATR or other techniques to identify the gas content of the liquid sample.

Although FIGS. 4 and 5 illustrate examples of methods 400 and 500 for automated measurements of gas content in liquid using in-situ sensors, various changes may be made to FIGS. 4 and 5. For example, while each figure shows a series of steps, various steps in each figure could overlap, occur in parallel, occur in a different order, or occur multiple times. Also, some steps could be omitted or moved. As an example, calibration could occur during raising and/or lowering of the piston head. As another example, in these figures, it is assumed that a measurement cycle begins with a raised piston head, although a measurement cycle could start at any other suitable point in each method. Further, in FIG. 4, any other suitable technique could be used to create a head space above a liquid sample, such as when the first valve is opened or closed at different times. In addition, any suitable technique could be used to analyze measurements to identify gas content of a liquid sample, such as NDIR, ATR, or other technique that is known in the art or later developed.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "transmit" and "receive," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system comprising:
    a signal source configured to provide a first signal for measuring a gas content of a liquid sample;
    an analyzer configured to determine the gas content of the liquid sample using a measurement of a second signal, the second signal based on the first signal; and
    an apparatus comprising:
        a walled structure having a cavity;
        a piston configured to (i) pull the liquid sample into the cavity and (ii) push the liquid sample out of the cavity, wherein the piston comprises a piston head having a reference material; and
        at least one measurement window having at least one inner surface exposed within the cavity, the at least one measurement window configured to (i) receive the first signal from the signal source and (ii) provide the second signal to the analyzer;
    wherein the signal source is further configured to provide a third signal to the at least one measurement window when the reference material is aligned with the at least one measurement window; and
    wherein the analyzer is further configured to be calibrated using a measurement of a fourth signal, the fourth signal comprising the third signal after the third signal has interacted with the reference material.

2. The system of claim 1, wherein:
    the piston is configured to repeatedly pull liquid samples into the cavity and push the liquid samples out of the cavity; and
    the analyzer is configured to determine the gas content of each of the liquid samples.

3. The system of claim 1, wherein the at least one measurement window comprises:
    a first measurement window configured to pass the first signal from the signal source into the cavity; and
    a second measurement window configured to pass the second signal from the cavity to the analyzer.

4. The system of claim 3, further comprising:
    at least one valve configured to create a head space containing air between the liquid sample and the piston head;
    wherein the first measurement window is configured to pass the first signal from the signal source into the head space; and
    wherein the second measurement window is configured to pass the second signal from the head space to the analyzer.

5. The system of claim 4, wherein the analyzer is configured to determine a gas content of the air in the head space, the gas content of the air related to the gas content of the liquid sample.

6. The system of claim 1, wherein the at least one measurement window comprises:
    a single measurement window configured to receive the first signal from the signal source and to provide the second signal to the analyzer.

7. The system of claim 6, wherein:
    the single measurement window comprises an Attenuated Total Reflection (ATR) crystal; and
    the analyzer is configured to identify an attenuation of the second signal with respect to the first signal in order to determine the gas content of the liquid sample.

8. The system of claim 1, wherein:
    the piston comprises a piston head having a seal; and
    the apparatus is configured such that movement of the piston head in the cavity causes the seal to push contaminants off the at least one inner surface of the at least one measurement window.

9. A system comprising:
a signal source configured to provide a first signal for measuring a gas content of a liquid sample;
an analyzer configured to determine the gas content of the liquid sample using a measurement of a second signal, the second signal based on the first signal; and
an apparatus comprising:
a walled structure having a cavity;
a piston configured to (i) pull the liquid sample into the cavity and (ii) push the liquid sample out of the cavity;
first and second measurement windows each having an inner surface exposed within the cavity; and
multiple valves configured to create a head space containing air between the liquid sample and the piston;
wherein the first measurement window is configured to pass the first signal from the signal source into the head space;
wherein the second measurement window is configured to receive the second signal from the head space; and
wherein the multiple valves comprise:
a first valve configured to trap the air in a space between a piston head of the piston and a flange; and
a second valve configured to allow the trapped air to move through the piston head.

10. An apparatus comprising:
a walled structure having a cavity;
a piston configured to (i) pull a liquid sample into the cavity and (ii) push the liquid sample out of the cavity, wherein the piston comprises a piston head having a reference material; and
at least one measurement window having at least one inner surface exposed within the cavity, the at least one measurement window configured to (i) receive a first signal for measuring a gas content of the liquid sample and (ii) provide a second signal, the second signal comprising the first signal after the first signal has interacted with material in the cavity and varying based on the gas content of the liquid sample;
wherein the at least one measurement window is further configured to (iii) receive a third signal when the reference material is aligned with the at least one measurement window and (iv) provide a fourth signal, the fourth signal comprising the third signal after the third signal has interacted with the reference material.

11. The apparatus of claim 10, wherein the at least one measurement window comprises:
a first measurement window configured to pass the first signal into the cavity; and
a second measurement window configured to receive the second signal from the cavity.

12. The apparatus of claim 11, further comprising:
at least one valve configured to create a head space containing air between the liquid sample and the piston head;
wherein the first measurement window is configured to pass the first signal into the head space; and
wherein the second measurement window is configured to receive the second signal from the head space.

13. The apparatus of claim 10, wherein the at least one measurement window comprises:
a single measurement window configured to receive the first signal and to provide the second signal.

14. The apparatus of claim 13, wherein the single measurement window comprises an Attenuated Total Reflection (ATR) crystal.

15. The apparatus of claim 10, wherein:
the piston comprises a piston head having a seal; and
the apparatus is configured such that movement of the piston head in the cavity causes the seal to push contaminants off the at least one inner surface of the at least one measurement window.

16. An apparatus comprising:
a walled structure having a cavity;
a piston configured to (i) pull the liquid sample into the cavity and (ii) push the liquid sample out of the cavity;
first and second measurement windows each having an inner surface exposed within the cavity; and
multiple valves configured to create a head space containing air between the liquid sample and the piston;
wherein the first measurement window is configured to pass the first signal into the head space;
wherein the second measurement window is configured to receive the second signal from the head space; and
wherein the multiple valves comprise:
a first valve configured to trap the air in a space between a piston head of the piston and a flange; and
a second valve configured to allow the trapped air to move through the piston head.

17. A method comprising:
pulling a liquid sample into a cavity of a sensor using a piston, the piston comprising a piston head having a reference material;
providing a first signal from a signal source into the cavity using at least one measurement window, the at least one measurement window having at least one inner surface exposed within the cavity;
providing a second signal to an analyzer using the at least one measurement window, the second signal comprising the first signal after the first signal has interacted with material in the cavity and varying based on a gas content of the liquid sample;
pushing the liquid sample out of the cavity using the piston;
providing a third signal from the signal source to the at least one measurement window when the reference material is aligned with the at least one measurement window; and
providing a fourth signal to the analyzer, the fourth signal comprising the third signal after the third signal has interacted with the reference material.

18. The method of claim 17, further comprising:
cleaning the at least one inner surface of the at least one measurement window using the piston.

19. The method of claim 17, further comprising:
creating a head space containing air between the liquid sample and the piston head;
wherein providing the first signal comprises providing the first signal into the head space; and
wherein providing the second signal comprises receiving the second signal from the head space.

20. The method of claim 19, wherein creating the head space comprises:
using a first valve to trap the air in a space between the piston head and a flange; and
using a second valve to allow the trapped air to move through the piston head.

* * * * *